(12) United States Patent
Phung et al.

(10) Patent No.: US 6,776,787 B2
(45) Date of Patent: Aug. 17, 2004

(54) SURGICAL PUNCH DEVICE

(76) Inventors: Trinh D. Phung, 63 Bambury La., Attleboro, MA (US) 02703; Douglas W Moore, 1625 High St., Westwood, MA (US) 02090; Jason LaShun Hamilton, 448 N. Main St., Providence, RI (US) 02904

( * ) Notice: Subject to any disclaimer, the term of this patent is extended or adjusted under 35 U.S.C. 154(b) by 0 days.

(21) Appl. No.: 09/971,421

(22) Filed: Oct. 5, 2001

(65) Prior Publication Data

US 2003/0069595 A1 Apr. 10, 2003

(51) Int. Cl.[7] .............................................. A61B 17/34
(52) U.S. Cl. ........................................ 606/185; 604/22
(58) Field of Search ................................ 606/167, 159, 606/180, 184, 185, 170; 600/566, 567

(56) References Cited

U.S. PATENT DOCUMENTS

| | | | | |
|---|---|---|---|---|
| 4,018,228 A | * | 4/1977 | Goosen | 606/184 |
| 4,216,776 A | | 8/1980 | Downie et al. | 128/305 |
| 5,129,913 A | | 7/1992 | Ruppert | 606/184 |
| 5,192,294 A | * | 3/1993 | Blake, III | 606/184 |
| 5,403,338 A | | 4/1995 | Milo | 606/184 |
| 5,488,958 A | | 2/1996 | Topel et al. | 128/754 |
| 5,569,276 A | * | 10/1996 | Jang et al. | 606/159 |
| 5,827,316 A | * | 10/1998 | Young et al. | 606/185 |
| 5,910,153 A | * | 6/1999 | Mayenberger | 606/184 |
| 6,080,176 A | * | 6/2000 | Young | 606/185 |
| 6,250,858 B1 | * | 6/2001 | Salyer | 408/239 R |

* cited by examiner

Primary Examiner—Vy Q. Bui
Assistant Examiner—Victor X Nguyen
(74) Attorney, Agent, or Firm—Dechert, LLP; John W. Ryan

(57) ABSTRACT

A device for forming openings (holes) in internal bodily tissue is provided. The device includes a cutter defining a longitudinal passageway and a cutting edge. The device also includes an inner core in reciprocally sliding relationship with the cutter having a tissue engagement portion at its distal end. A syringe-like mechanism moves the cutter and the core substantially co-axially between a first position wherein the distal portion of the core extends distally of the cutting edge and a second position wherein the distal portion of the core resides within the passageway. Tissue is sheared as the core and cutter are moved from the first to the second position. The core and cutter are attached to different portions of the syringe-like mechanism such that the longitudinal axes of the cutter passageway, the core member and the activation assembly may deviate (i.e., "float") relative to one another.

22 Claims, 8 Drawing Sheets

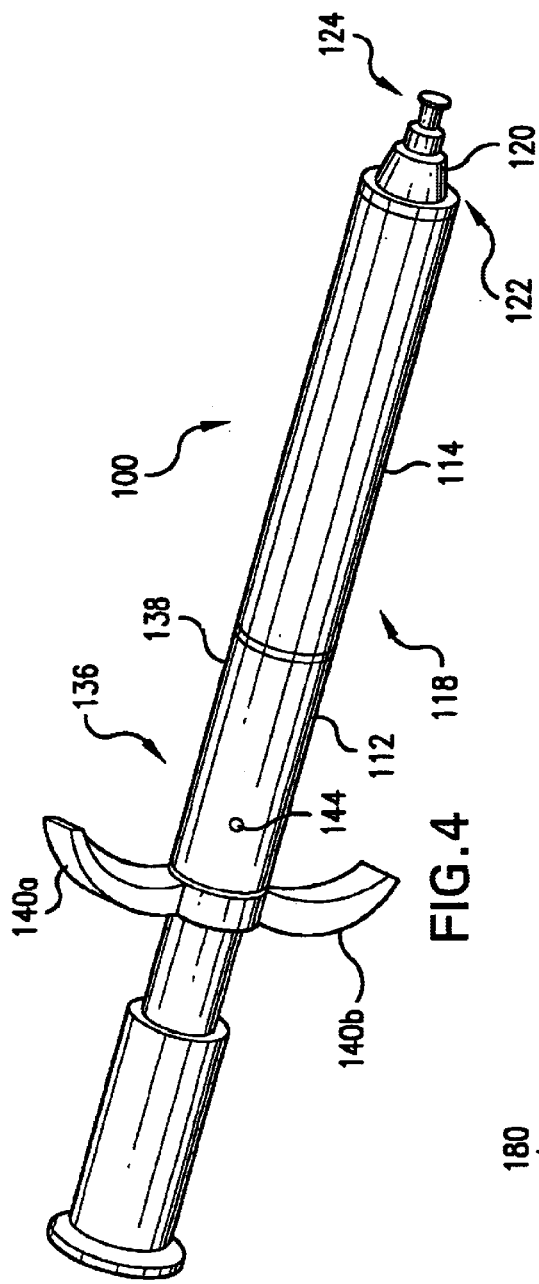
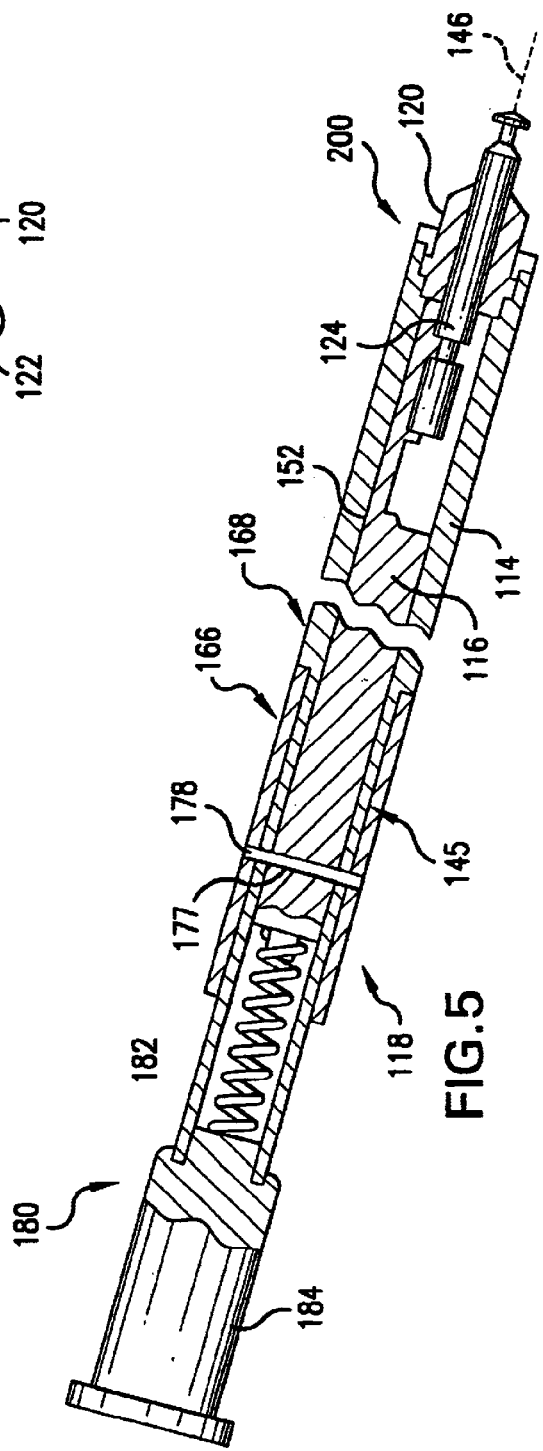
FIG. 4
FIG. 5

SURGICAL PUNCH DEVICE

BACKGROUND

1. Field of Invention

The present invention relates generally to surgical devices. More particularly, the present invention relates to surgical punch devices for the formation of well-defined holes in blood vessel walls (or other internal bodily tissue layers) during the course of a surgical procedure. Still more particularly, the present invention relates to improvements in surgical punch devices that reduce the levels of applied force required to punch out tissue plugs from tissue walls, and that otherwise improve the operational characteristics of the device.

2. Summary of the Prior Art

Surgical punch devices for forming holes through bodily tissue layers during the course of surgical procedures per se are generally well known in the art. Representative examples of some of the various versions of known surgical punch devices are shown in the following United States Patents (the disclosures of which are hereby incorporated by reference into this specification): U.S. Pat. Nos. 4,018,228; 4,216,776; 5,129,913; 5,192,294; 5,403,338; 5,488,958; and 5,827,316.

The basic concept of surgical punch devices is to provide a device including a pair of externally operable, reciprocally interacting, elongate elements for the formation of a hole through an internal tissue layer at an internal surgical site easily and simply during the course of a surgical procedure. The devices heretofore utilized to accomplish this goal typically included an elongate outer sheath having a distally facing sharpened edge, and an elongate plunger-like member disposed within the outer sheath. The plunger-like member was designed for the reciprocating movement of its distal end from a normally extended position relative to the sharpened edge of the outer sheath into the distal portion of the outer sheath in response to external manipulation of an activation mechanism associated with the proximal portions of the outer sheath and the plunger-like member respectively. The plunger-like member also typically included structure designed to receive tissue while its distal end portion was extended out of the distal end of the outer sheath. Further, the plunger-like member was contemplated to fit tightly enough within the outer sheath that received tissue could be caused to be sheared away from the adjoining tissue layer as the plunger-like member was caused to move past the distally facing sharpened edge of, and into, the outer sheath by the external activation mechanism. (Obviously, the relative movement of the outer sheath and the plunger-like member just described also could be considered as the outer sheath moving relative to the plunger-like member, or as the outer sheath and the plunger-like member moving simultaneously in opposite directions relative to each other without changing the basic operational characteristics of the device.)

Various structural modifications also have been provided to this basic surgical punch device in the prior art.

For example, the outer sheath and the plunger-like member have been interconnected with one another in various ways so as to cause them to rotate relative to each other as they are moved from the normal plunger extended position to the plunger retracted position, and vice versa. This modification introduces a slicing component to the cutting out of a section of a tissue layer contemplated by the basic surgical punch concept. The purpose of this modification is to reduce the level of applied force required to remove a cut out tissue portion (plug) from its adjoining tissue layer.

Further, numerous activation mechanisms for causing the desired relative movement between the outer sheath and inner plunger have been proposed with varying degrees of success. In addition, it is common in surgical punch devices to use a separate cutting blade mounted at the distal end of the outer sheath to provide the distally facing cutting edge, instead of simply sharpening the distal end of the outer sheath. Other modifications of the basic surgical punch device are described in the above-referred-to United States Patents and/or will become apparent as the present discussion proceeds.

A typical example of the heretofore known structure and use of surgical punch devices will be better understood with reference to the following brief discussion of the procedures and requirements of coronary by-pass surgery. It is to be understood, however, that this usage context is presented herein by way of illustrative example only, and that surgical punch devices may, and do, find other usage contexts satisfying other specific requirements.

The goal in coronary by-pass procedures is to create an open blood flow passageway around one or more diseased, blocked or partially occluded coronary arteries so as to ensure appropriate blood flow to the heart muscle. Without such blood flow, the heart muscle may be damaged and/or cease to function appropriately. Hence, if the condition is not corrected, the result may be a heart attack or, in extreme cases, death to the patient.

To accomplish the desired by-pass, it is conventional to use a saphenous vein graft to create an alternative pathway for the flow of blood to the heart muscle. Specifically, an opening (i.e., hole) is formed in the wall of the ascending aorta. Thereafter, the proximal end wall of the graft is anastomosed (attached) around the periphery of the opening in a tight, sealing manner (typically by suturing). The distal end of the graft is then affixed in a similar manner to the periphery of a hole formed in the subject artery downstream from the diseased portion, blockage or occlusion.

The formation of the desired openings in the walls of the involved blood vessels (as parenthetically suggested above) must be understood as involving the creation of open holes in the blood vessel walls. The reasons for this are clear to those skilled in the art. It is only by the formation of open holes that an unobstructed flow of blood through the graft can be insured. The creation of slits, cuts, punctures or the like are not satisfactory. This is primarily because internal bodily tissue demonstrates a tendency to close in upon itself after the passage of a knife-like blade or awl-like device through it. Therefore, it is only by the actual removal of tissue from the blood vessel wall that the presence of a continuously open passageway may be assured.

Accordingly, it has become conventional in the art that the formation of the desired openings (holes) through the blood vessel walls involves the creation of "pilot opening", i.e., a small, slit-like cut or opening through the tissue of the blood vessel wall, often using either a scalpel or scissors. Thereafter, a surgical punch device typically is used to form the desired well-defined hole in the blood vessel wall. This procedure has been found to facilitate the attachment of grafts to blood vessel walls in the desired relationship. It also has been found to aid in the avoidance of complications such as leakage from the attachment site and/or the presence of loose tissue pieces within the hole and/or adjoining blood vessel lumens that could break away and be carried in the bloodstream causing damage or blockages elsewhere within the patient. It also facilitates the removal of punched out tissue from the interior of the patient.

An illustrative version of a conventional surgical punch useful in surgical procedures of the type just summarized is illustratively shown in FIG. 1. Generally speaking, the surgical punch 2 includes an anvil or other support portion 4 formed and/or located at the distal end 6 of a core member (rod) 8. The core member 8 in turn is disposed in telescoping, and generally co-axial, engagement within a generally cylindrical member (outer sheath) 10. Accordingly, the surgical punch may be very much syringe-like in appearance.

Further, while the internal linkage mechanisms inherent in surgical punch devices are different from a common syringe (i.e., distal pushing on the proximal end of the plunger while pulling on finger engagement elements moves the plunger proximally relative to the outer sheath instead of distally relative thereto) the external operating characteristics thereof are very similar to the well-known syringe. Therefore, since conventional surgical punch devices may be operated by a surgeon in much the same manner as a common syringe, and since such devices also produce readily predictable reactions at their distal ends in direct correspondence to applied movements to the parts at their respective proximal ends, conventional surgical punch devices have found ready acceptance in the art.

In addition, with the core member 8 in its normal distal-most position relative to the outer sheath 10, the anvil or support 4 is adapted for insertion into the blood vessel (such as, for example, the aorta) through the small opening formed in the tissue defining its wall by the scalpel or scissors referred to above. Then, as will appear more fully below, the part of the aorta wall surrounding the original cut ("pilot opening") lodges itself in the recessed portion 12 in the core member (rod) 8 located between the anvil 4 and the proximally extending main part 16 of the core member (rod) 8. (See, FIG. 2)

The surgeon then grasps the surgical punch 2 in much the same manner as he/she would grasp a conventional syringe. Thereafter, when he/she approximates his/her thumb and first and second fingers the result is the exertion of a pushing force on a thumb button 18 and the exertion of a pulling force on the finger support 20. This interaction between the surgeon's hand and the surgical punch device 2 causes the distal end 6 of the core member (rod) 8 to move proximally into the substantially cylindrical member (outer sheath) 10 at its sharpened distal end (blade edge) 22. The desired result of this manipulation is that tissue trapped in the recessed area 12 is sheared away from the adjoining blood vessel (aortal) wall leaving a plug of tissue within the device. The surgical punch device then may be removed from the patient leaving a comparatively large and well-defined hole in the blood vessel (aortal) wall.

Numerous problems remain, however. For example, the tissue of the aorta wall consists of three layers as generally shown in FIG. 2, one of which (known as the "adventitia") 24 being notoriously fibrous and resilient in nature. Therefore, the tissue of the aorta wall is difficult to sever by shearing cleanly, smoothly and without the need for the application of significant force. More specifically, it will be readily apparent that the shearing of a fibrous and resilient tissue layer along the entire circumference of a hole to be formed therein at the same time is difficult.

One reason for this is that the fit between the cutting edge 22 and the rod 8 typically cannot be made tight enough to assure that the blade rides directly against the outer surface of the rod. In practice, a small gap must be present between the sheath and the outer surface of the rod. This gap is necessary in order to assure that the rod rides satisfactorily in reciprocally movable relation within the sheath. It also is necessary in order to assure that the alignment of the axis of the surgical punch with the tissue wall to be punched can be made as close to perpendicular as possible.

The presence of this gap, on the other hand, allows an undesirable stretching of the fibrous and resilient tissue between the sheath and the rod prior to its being cut by the blade. Therefore, it will recognized that conventional surgical punch devices introduce inconvenient operational distractions during delicate heart surgery and/or similar procedures that may adversely impact the ultimate surgical result. It also has been found that when conventional surgical punch devices are used, there is a tendency for the edges of the hole in the target tissue formed by the punch device to be either rough or frayed (at least microscopically). As mentioned, rough or frayed hole edges can lead to leakage at the joinder of the graft to the aortal wall and/or to the undesirable breakaway of loose material from the aortal wall with resultant potentially problematic conveyance of the same in the bloodstream.

Further, if the tightness of the fit is too great, the result is that the surgeon is faced not only with overcoming the toughness and resilience of the tissue being punched, but also the frictional engagement of the core and the cutting blade. If the tightness of the fit is too loose, however, the tough and resilient nature of the aorta wall tends to stretch the tissue between the cutting blade edge and the outer edge of the distal end of the recessed portion of the core. The resultant definition of the boundary of the hole so formed consequently is not fine in nature, and the applied force required to form the punch out is substantial. In addition, binding between the outer sheath and the rod can become an issue in some cases due to the non-co-axial alignment of their axes of movement relative to one another.

To date, several alternatives have been presented in the art attempting to deal with the foregoing problematic issues. In one of these alternatives (already mentioned), a relative rotation between the cutting blade (outer sheath) and the core (rod) is created as they are moved in opposite directions relative to each other. This results in the hole in the blood vessel wall being formed by more of a circumferential slicing motion of the parts than by a perpendicular shearing action between the parts. This alternative in some cases may improve the smoothness of the hole walls, but at the same time, it undesirably increases in the complexity and cost of the required activation mechanism.

Serrations also have been added to the cutting edge to facilitate the cutting action. The result, however, is a rougher hole edge with little significant improvement in the overall operative characteristics of the device.

Another alternative (illustratively depicted in FIG. 3) that has been utilized in the prior art involves allowing the longitudinal axis of a cutting blade element mounted at the distal end of the outer sheath to "float" (i.e., to shift slightly longitudinally, radially and/or both simultaneously) relative to the longitudinal axis of the outer sheath. This alternative has the advantage of tending to allow the cutting edge of the cutting blade element to "find its own center" with regard to the anvil or support as the distal end of the core is being retracted into the cutting blade/outer sheath to punch out a tissue plug. There are detrimental trade offs, however.

For example, the elongate core, generally indicated at 40, is commonly formed of rigid material such as metal, and as a single piece. This core typically extends through the outer sheath 42 that in turn carries a cylindrical cutting blade 44 rigidly affixed to the outer sheath co-axially at its distal end 48. Alternatively, the core of some surgical punches have been formed by a plastic core portion 50 located within the outer sheath 42 and a machined metallic distal core portion 52 insert molded to the distal end 54 of the plastic core 50. When this is done, at least one circumferential recess 56 is typically formed in the machined metallic core portion 52 distally of its proximal end 58 in order to assure a firm and rigid attachment of the plastic and metallic core portions.

Of course, in the latter alternative, the anvil and adjacent distal recessed structure are formed in the machined metallic core portion that extends through the cutting blade 44. In either event, the distal end surface 60 of the outer sheath 42 may be designed to include first, second and third counterbores 62, 64 and 66, respectively, of successively decreasing depth and successively increasing diameter. This configuration, in combination with an end ring cap 68, allows the cutting blade 44 to "float" relative to the outer sheath 42 in the manner shown in FIG. 3.

The longitudinally hollow cutting blade 44 includes a distally pointed end section 70, a substantially constant diameter proximal section 72, and a mid-section 74 having a diameter larger than the diameter of either the proximal section or the distal section so as to form what may be loosely referred to as an outwardly projecting belt or ridge around the cutting blade 44. The lengths and diameters of the various portions of the cutting blade 44, and of the respective counterbores 62, 64 and 66 are related to each other in such a way that the cutting blade 42 "floats" within the distal end 60 of the sheath 44 when the ring cap member 68 is inserted proximally into the disalmost counterbore 66.

More specifically, the diameter of counterbore 60 is slightly greater than the diameter of the proximal section 72 of the cutting blade 44, and the length of the counterbore 60 is slightly greater than the combined length of the proximal section 72 and mid section 74 of the cutting blade 44 plus the portion of ring cap 68 engaging counterbore 66. Similarly, the diameter of counterbore 62 is slightly greater than the diameter of the mid-section 74 of the cutting blade 44, and the length of counterbore 62 is slightly greater than the length of the mid-section 74 of the cutting blade 44 plus the portion of ring cap 68 engaging counterbore 66.

Thus, in the assembled cross-sectional configuration shown in FIG. 3, a plastic inner core 50 extends in sliding relation through the majority of the outer sheath 42. At the distal end of the plastic core, the stainless steel core 52 is rigidly and co-axially attached to the plastic core 50 and extends distally and rigidly outwardly from the distal end 54 of the outer sheath 42.

The cutting blade 44 receives the stainless steel core 52 in sliding relationship while at the same time being disposed in the "floating" relationship with respect to the counterbores 62, 64 and 66 as discussed above. This has been found to partially alleviate alignment problems arising from the cutting blade edge engaging the outer blood vessel wall while the distal recess wall engages the inner blood vessel wall, but at the expense of several further trade-offs.

Since the cutting blade is allowed to "float", it is not possible to perform the punching operation by slicing the tissue by the relative rotation of the outer sheath and the inner core structure. Further, the problems inherent in misalignment (and hence a dragging frictional engagement) between the cutting blade and the inner core remains, as do those associated with the complexity and expense of insert molding a plastic inner core in co-axial relationship to a metallic core passing through the cutting blade.

In addition, surgeons have experienced difficulty in removing punched out tissue plugs from the main body/cutter blade of conventional surgical punch devices. This is important because a surgeon typically desires to form a plurality of holes in the aorta at substantially the same point in a multiple heart by-pass surgical procedure. Hence, difficulty and/or delay in clearing the punch of previously punched out tissue is undesirably time-consuming and frustrating, particularly in the time-sensitive context of open-heart surgical procedures. The reasons for these problems will appear below in connection with alternative embodiments of the invention designed to alleviate or remove them from the operational characteristics of the novel surgical punch device herein described and claimed.

SUMMARY OF THE INVENTION

Accordingly, it is an object of the present invention to provide a surgical punch device wherein the cutting mechanism and the activation mechanism are distinct but interconnected elements, and the entire cutting mechanism is self-aligning relative to both the activation mechanism and the tissue to be punched.

It also is an object of the present invention to provide a surgical punch device that provides a smooth edged cut without the distraction of noticeable rubbing or catching between the parts thereof and/or with tissue.

Further, it is another object of the invention to provide a surgical punch device wherein the cutting blade and the anvil/support carrying inner core portions of the cutting mechanism respectively "float" separately relative to the outer sheath and inner rod of the activation mechanism.

Still further, it is an object of the above invention to provide a surgical punch device that may be made either in a disposable or in a re-usable form according to the preference of the user, cost considerations and/or the desired robustness of construction among other factors.

Yet another object of the invention is to provide a surgical punch device having an improved cutting blade designed for piercing tissue to be removed by the surgical punching device at preselected circumferentially spaced locations about the plug of tissue to be punched out prior to shearing the circumferential tissue located along the desired plug periphery between the pierced locations.

Still another object of the invention is to provide a surgical punch device wherein rough and/or frayed edges of a punched out plug do not interfere with the ease of removal of a punched out tissue plug from the interior of the surgical punch device.

In summary, a device for forming openings in internal bodily tissue such as blood vessels or the like during the course of surgical procedures such as by-pass surgery is provided. The device includes a cutting blade having a body portion defining a longitudinal passageway and a substantially distally facing cutting edge. The device also includes an inner core disposed in reciprocally sliding relationship with the passageway of the cutting blade. The inner core has a support portion at its distal end, and a tissue engagement portion located proximally adjacent to the distal support portion. In addition, an activation mechanism including an outer sheath and inner core, often in a generally syringe-like configuration, is provided for moving the cutting blade and the inner core generally co-axially relative to one another.

Specifically, the movement of the cutting blade and the inner core is contemplated to be between a first position wherein the distal portion of the core extends distally of the cutting edge of the cutting blade, and a second position wherein the distal portion of the core resides within the passageway of the cutting blade. The passageway of the cutting blade and the inner core are sized relative to one another such that a plug of tissue received by the tissue engagement portion may be sheared away from the adjoining tissue as the inner core and cutting blade are moved from their first relative positions to their second relative positions.

In addition, the inner core and cutting blade are respectively attached to different reciprocally moving portions of the activation mechanism. This connection is made in such a manner that the respective longitudinal axes of the cutting blade passageway and the outer sheath portion of the syringe-like activation mechanism on the one hand, and the inner core member and the plunger portion of the activation mechanism on the other hand may substantially freely deviate (i.e., "float") to a limited extent relative to one another as the core member and the cutting blade are moved from their first relative positions to their second relative positions by manipulation of the activation assembly.

More specifically, the present invention proceeds from the realization that it is the relationship of the cutting blade and the inner core extending therethrough so as to directly interact with the cutting blade that controls the ultimate functional characteristics and results of the use of a surgical punch device. In particular, it is interactions between portions of the device at locations removed from the cutting blade/inner core mechanism that cause the problems referred to above in the cut away of a tissue plug from a tissue layer. Hence, it has been found that a surgical punch device may be accurately characterized as a combination of an activation mechanism including syringe-like components with a separate cutting apparatus including a co-axially aligned cutting blade and reciprocally movable core member. Further, it has been found that by modifying a conventional surgical punch in accordance with this novel characterization, a significantly improved device results.

Accordingly, the foregoing and other objects, features and advantages of the present invention are accomplished by the provision of a substantially conventional surgical punch device in which the attachment of a tissue receiving core portion extending through the cutting blade is modified so as to allow the core portion to "float" relative to its attachment to the distal end of the plunger-like portion of the activation assembly. In this way, the core portion and the cutting blade of what sometimes will be referred to hereinafter as the "cutting assembly" may be disposed in separate so-called "floating" relationships to the respective longitudinal axes defined by the outer sheath and the inner plunger-like portions of the activation assembly. This, in turn, leads to the avoidance of the phenomenon of a dragging resistance experienced by users of prior versions of surgical punch devices both with, and without, "floating" cutting blades. In addition, the resulting device is more easily operated, and the resulting punched hole in tissue is more accurately and cleanly cut.

Also, in some embodiments, a substantially triangular cross-sectional portion of the distal portion of the outer anvil/support wall at its outer periphery may be removed. By so doing, the outer anvil/support wall becomes close to pointed at its proximal end and tapers inwardly as it extends from its proximal end toward its distal end. This configuration presents less resistance to the passage of the tissue stretched during the punching operation discussed above. It also provides a channel-like cavity into which the previously stretched tissue can collect without causing binding against the inner wall of the cutting blade as the core is moved distally relative to the cutting blade to free a previously cut tissue plug. Therefore, more previously stretched tissue can work its way between the anvil/support and the inner cutting blade wall as the core is moved distally relative thereto. Also, the previously stretched tissue that heretofore tended to bunch up at the distal end of the gap between the anvil/support and the inner cutting blade wall is provided with room within which to gather in a manner that does not exert significant resistance against the inner cutting blade wall.

Similarly, the diameter of the distally facing ledge of the main portion of the metal core that forms a wall of the recessed portion may be reduced and the outer wall of the main portion of the metallic core gradually tapered (or more sharply tapered) proximally and outwardly from the periphery of the so reduced diameter of the distally facing ledge. In this embodiment, the tapering continues until the outer wall of the main portion of the metal core reaches its original diameter (i.e., generally slidingly engaging the inner wall of the outer sheath/cutting blade).

The latter configuration provides an open, substantially triangular cross-sectioned channel into which tissue that formerly caused binding between the machined metal core and the inner wall of the cutting blade may collect. In this manner, rough and/or ragged tissue plug edges are prevented from introducing undesirable resistance to the free distal movement of the metal core relative to the inner wall of the cutting blade for the removal of punched out tissue from the interior of the tool. Still further, the addition of a surgically inert lubricating or friction reducing coating material onto the distally extending portion of the main machined metal core is contemplated as an option to further reduce sticking.

Additional embodiments of the invention also are contemplated. In one such embodiment, the distal cutting edge of the cutting blade is formed as four or more cut away sections substantially equally spaced relative to one another along the circumference of the cutting edge. More particularly, starting from the conventional circular cutting edge disposed in a plane perpendicular to the axis of the cutting blade, a preselected number of point locations may be selected, usually in substantially equally spaced relation to one another about the periphery of the cutting edge. Thereafter, material may be removed from the cutting blade element between the preselected points such that corresponding new curved cutting blades are formed between each pair of preselected points. Each of the corresponding new curved cutting blades follows the inner wall of the cutting blade element in circumferential relation to the cutting blade as well as a corresponding curve in axial relation to the cutting blade.

In this way what may be referred to as a scalloped cutter blade edge may be created at the distal end of the cutting blade, with each scallop being the same as those adjacent thereto. The concept of this embodiment is that the various points will tend to pierce the tough and resilient tissue layer of the aorta wall, and that the cutting edges between the points thereafter will sever the aorta wall tissue layers between the pierced locations. Hence, the aorta wall tissue will be more accurately and cleanly severed, rather than stretched, by the cutting blade assembly. Also, the tissue plugs will be punched out with cleaner edges under the exertion of less applied force. Still further, a cutting edge similar to that just described may be formed along the outer proximal edge of the anvil either alone, or in combination with, the above-described cutting blade configuration, if desired.

BRIEF DESCRIPTION OF THE DRAWINGS

The invention will be better understood by those skilled in the art from the following description of the presently preferred embodiments thereof. It is to be understood that the specific embodiments of the invention described are intended to be illustrative of the best mode of practicing the invention currently known, and not to be limiting of the invention except to the extent necessary to the understanding of the appended claims. This detailed description is rendered for clarity in conjunction with the appended drawings in which:

FIG. 4 is a perspective view of an illustrative surgical punch in accordance with the present invention;

FIG. 5 is a perspective view of one embodiment of the present invention in partial cross-section;

DETAILED DESCRIPTION OF PREFERRED EMBODIMENTS

Figure 1:
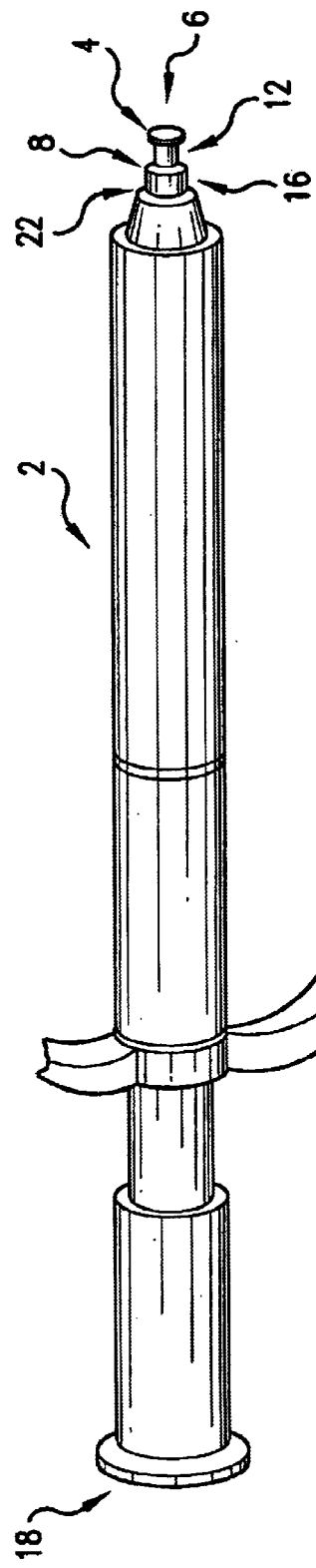
FIG. 1 is a perspective view of a conventional surgical punch device.
Figure 2:
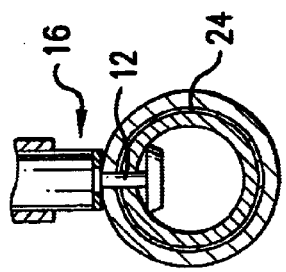
FIG. 2 is an illustrative, cut-away, side view in partial section showing the engagement of a distally disposed anvil/support portion of a core within an aortic blood vessel during the course of the punching of a hole in the blood vessel wall.

Referring now to the drawings, and particularly to FIG. 4, there is shown a perspective view of a representative surgical punch device in accordance with the present invention. The surgical punch device 100 is substantially similar to the prior art surgical punch device shown in FIG. 1. Specifically, it is generally syringe-like in external appearance and external operational characteristics so as to facilitate one-handed use by a surgeon. In this regard, it will be understood by those skilled in the art that prior surgical punch devices were fairly basic in concept. By this it is meant that conventional surgical punch devices were primarily simply a means to form a hole in a tissue layer (often at a small operative site) from a distance. As such, they consisted generally of an outer sheath and an inner plunger-like member adapted to be moved reciprocally with respect to one another in a generally syringe-like configuration. Thus, in a plunger extended position (FIGS. 1 and 4), the plunger was adapted to be inserted through a tissue layer and to receive tissue in a recess adjacent its distal end (FIG. 2). Further, the elements of the device were designed to interact in such a manner that a plug of tissue would be cut out of a target tissue layer by retracting the distal portion of the plunger into the outer sheath. The operational concept of the present invention, on the other hand, is similar but significantly more sophisticated.

As alluded to above, various mechanisms for controlling to relative movement of the outer sheath and the plunger-like element (rod) utilized as an activation means for controlling the relative movement of operative elements at a distance are known in the art. Accordingly, only the basics of a preferred version of an activation mechanism for use in this invention will be set forth in detail below. Further detail regarding such mechanisms is readily available in the prior art referred to above and elsewhere.

Figure 6:
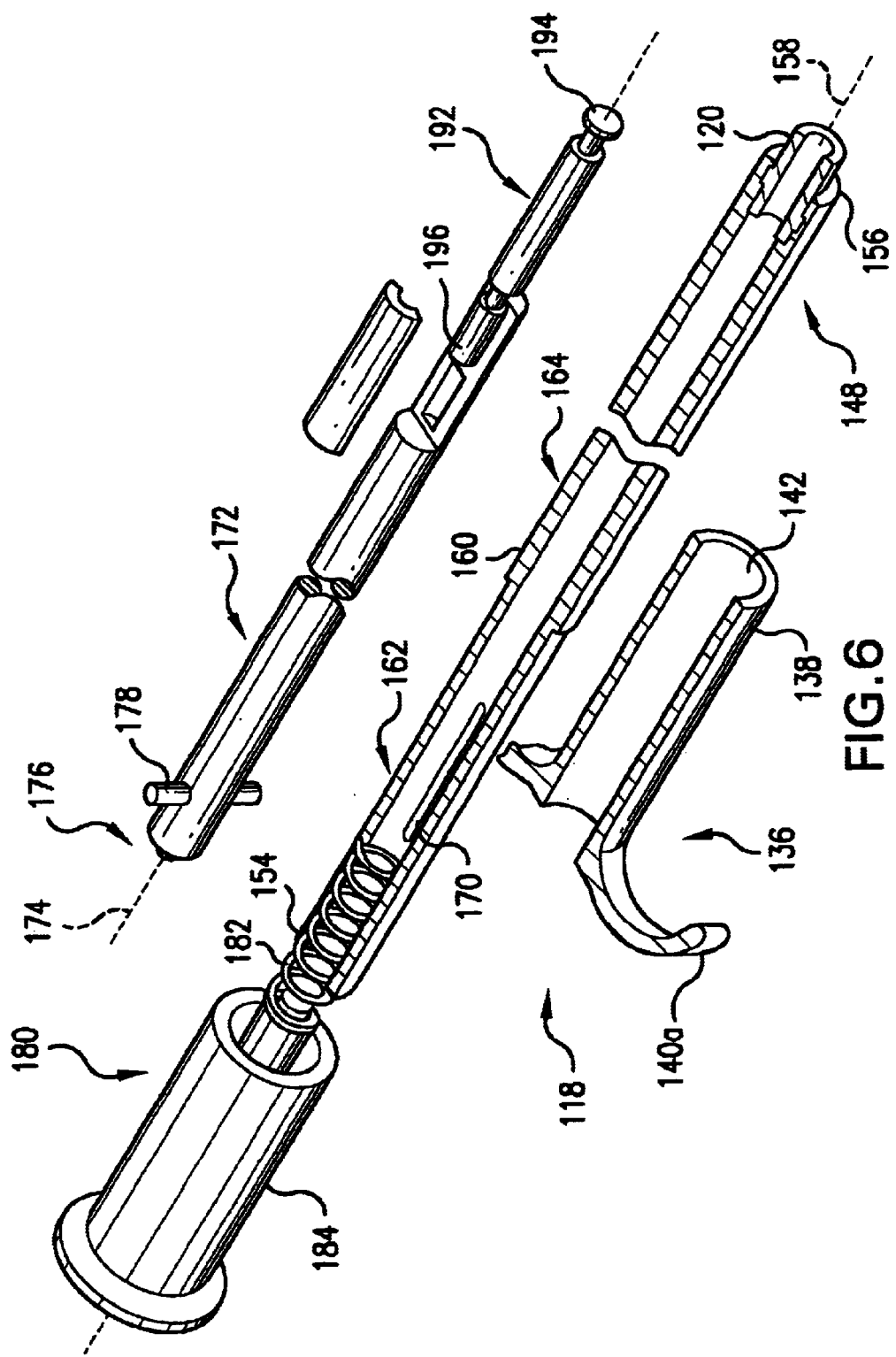
FIG. 6 is an exploded view of the exemplary embodiment of the surgical punch depicted in FIG. 5.

Therefore, as will be seen in the representative embodiment of this invention shown in FIGS. 4–9, the surgical punch device 100 of the present invention generally includes a finger grip 112, an elongate hollow shaft 114, and a rod 116 assembled together to form an activation assembly, generally indicated at 118, and best seen in FIGS. 5 and 6. Further, a substantially tubular cutting blade 120 is located at the distal end 122 of the shaft 114, and a machined core member 124 defining an anvil-like support structure 126 separated from the remainder 128 of the machined core member 124 by a circumferential recessed portion 130 adjacent its distal end 132 is located in passageway 134 of cutting blade 120. The latter combination will be referred to sometimes hereinafter as "cutting assembly" 200.

Additional information concerning the preferred embodiment of each of these elements, and their interactive assembly with one another, will become apparent to those skilled in the art from the following more detailed description of preferred embodiments of the invention as depicted in the drawings. Significantly, however, unlike the prior art, the device of the invention also will be seen to constitute a novel interactive interconnection of an activation mechanism 118 and a distinct cutting assembly 200. In addition, certain other features that are particularly useful in the context of this novel combination also will be described.

Starting with the representative activation assembly 118 (FIGS. 5 and 6), it will be seen that a finger grip body 136 is provided. The finger grip body 136 includes a housing 138 from which finger seat portions 140a and 140b extend substantially radially outwardly and oppositely relative to one another. In the embodiment shown, finger seats 140a and 140b constitute a pair of opposing projections that are shaped for engagement by the fingers of the surgeon during the use of the device. It will be understood, however, that the finger seats may define substantially any outwardly projecting structure that can be engaged by the surgeon's fingers during the manipulation of the device without departure from this invention in its broadest aspects. Thus, for example, the finger seats might be a continuous outwardly extending projection (not shown) from housing 138 surrounding its periphery.

In addition, housing 138 includes inwardly facing wall portions 142 that define a central longitudinal opening 145 centered on a longitudinal axis 146. Still further, at least one opening 144 extends through walls 142 in a substantially radial direction relative to the longitudinal axis 146.

A longitudinally hollow shaft 148 (see also general reference numeral 114) is also provided. Shaft 148 is an elongate member including wall portions 150 defining an inner longitudinal passageway 152 extending from proximal end 154 to distal end 156 of shaft 148 centered relative to a longitudinal axis 158. The outer surface 160 of wall portions 150 includes a proximal portion 162 and a distal portion 164. The proximal portion 162 is molded or cut away relative to the slope defined by the distal portion 164 in a manner such that proximal portion 162 fits in sliding relation into and through the central longitudinal opening 145 of the housing 138 (FIG. 5). Typically, this fit is such that the outer surface 166 of housing 138 and the adjoining outer surface of 168 of the distal portion 164 of the surface 160 are in abutting alignment with one another (i.e., their outer edges match) when the elements of the device are in their normal positional relationship (see FIGS. 4 and 5) as discussed further below.

In addition, the proximal portion 162 of shaft 148 defines at least one slot 170 aligned with the at least one radial opening 144 through walls 142. The purpose of slot(s) 170 will become apparent below. The distal outer surface portion 164 of shaft 148, on the other hand, permissibly may taper inwardly as it extends from the proximal portion 162 toward the distal end of the shaft. The structure of the internal proximal and distal portions of the longitudinal passageway 152 will be discussed in further detail below.

A rod member (plunger) 172 (see also general reference numeral 116) also is provided. The rod 172 is shorter than central longitudinal passageway 152 and is centered on a longitudinal axis 174 for sliding motion in passageway 152. Ideally, longitudinal axes 158 and 174 would be co-axial, however, in practicality this is not generally the case. In addition, within proximal portion 176 of rod 172 an opening 177 extending at least partially through the rod is provided. Opening 177 is such that it may be aligned with slot(s) 170 and radial opening(s) 144 so as to permit a pin 178 to be inserted through opening 144 and slot 170 into rod member 172 (FIG. 5). Thus, as will be apparent to those skilled in the art from the foregoing description and the attached drawings, housing 138 and rod member 172 are joined in a manner such that they move together relative to shaft 148 a longitudinally measured distance equal to the longitudinal length of the slot 170.

To accomplish this relative movement, a motivation assembly 180 is provided. In the embodiment shown, motivation assembly 180 includes a helical spring 182 located in the proximal portion of the shaft 148, and an applied force receiving member 184 mounted on the proximal end of the shaft. The applied force-receiving member 184 may take substantially any desired form (such as, for example, the thumb button shown). Functionally, however, the force-receiving member 184 is designed for movement relative to the shaft from a first proximal position to a second distal position and is attached to the shaft. Therefore, it will be understood that the force receiving member 184 traps the helical spring in the shaft between itself and the proximal end of the rod 172. Accordingly, the spring normally biases the rod toward its distallmost position within the shaft and the force-receiving member 184 toward its proximalmost position relative to the shaft 148 (see FIGS. 1 and 4).

Therefore, it will be seen that in response to distally applied force against member 184, while housing 138 is subjected to proximally applied force against finger grips 140a and 140b, the rod member 172 and housing 138 joined by pin 178, on the one hand, and shaft 148 on the other hand are caused to shift longitudinal positions relative to one another. More specifically, as the finger grips are pulled and the force-receiving member is pushed, the proximal portion of the shaft slides into the corresponding longitudinal cavity in the force-receiving member against to expansion force of the spring. At the same time, the finger grip support housing slides proximally along the sheath to the extent allowed by the engagement of the pin with the slot. Thus, the final result is a smooth mutual movement of the force-receiving member and the finger grip support housing toward each other against the force of the spring. (See, FIGS. 5, 10 and 11)

Having thus described the basics of a typical activation mechanism, numerous additional details of its structure and operation will be apparent to those skilled in the art. In addition, numerous alternative structures for the accomplishment of the same motivational capabilities at a distance also will be readily apparent to those skilled in the art. The exact nature of this activation mechanism can be varied without departure from the invention in its broadest aspects. Therefore, the foregoing description of a specific structure for this purpose is to be understood as being illustrative only and in no way limiting of the scope of the present invention in its broadest aspects.

The distinct cutting assembly 200 of the present invention and its novel interrelated interconnected disposition relative to the activation mechanism now will be discussed.

Figure 7:
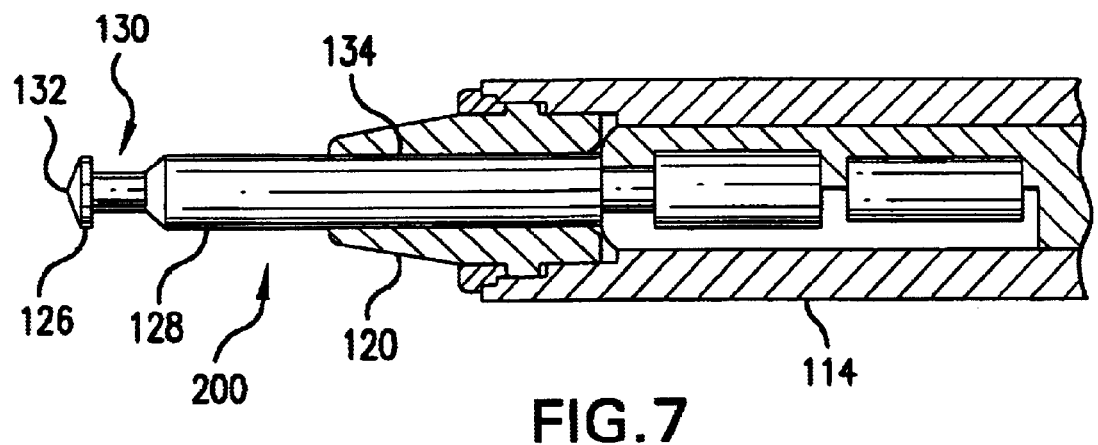
FIG. 7 is an enlarged, cut away, side view in partial section of the distal portion of the embodiment of the surgical punch device of the present invention depicted in FIGS. 5 and 6.
Figure 8:
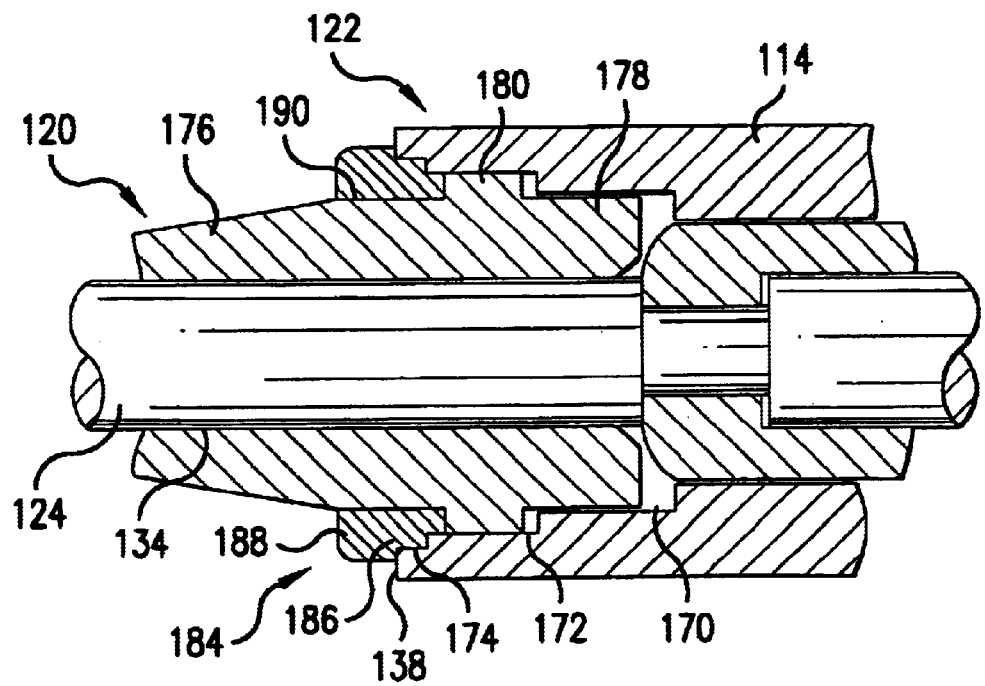
FIG. 8 is a further enlarged side cross-sectional view of the joinder of the cutting assembly and the activation mechanism of the embodiment of the invention shown in FIGS. 5 and 6.

The disposition of substantially tubular cutting blade 120 at the distal end 122 of the shaft 114 in the illustrative embodiments depicted in the drawings is substantially the same as that discussed above in connection with the "floating" version of the prior art. Thus, as best seen in FIGS. 7 and 8, the distal end 122 of the shaft 114 includes first, second and third counterbores 170, 172 and 174, respectively, of successively decreasing depth and successively increasing diameter. The longitudinally hollow cutting blade 120, on the other hand, includes a distal pointed end section 176, a substantially constant diameter proximal section 178, and a mid-section 180 having at least circumferentially spaced portions with a diameter larger than the diameter of either the proximal section or the distal section so as to form what may be referred to as an outwardly projecting belt or rib around the cutting blade 120. The lengths and diameters of the various portions of the cutting blade 120 and of the respective counterbores 170, 172 and 174 are related to each other such that the cutting blade 120 "floats" in the distal end of the shaft 114.

More specifically, the diameter of counterbore 170 is slightly greater than the diameter of the proximal section 178 of the cutting blade 120, and the difference in length between the counterbore 170 and the counterbore 172 is slightly greater than the length of the proximal section 178 of the cutting blade 120. Similarly, the diameter of counterbore 172 is slightly greater than the diameter of the mid-section 180 of the cutting blade 120, and the difference in length between the counterbore 172 and the counterbore 174 is slightly greater than the length of the mid-section 180 of the cutting blade 120. Further, a substantially cylindrical distal cap 184 is provided having a proximal portion 186 adapted to fill the counterbore 174, a distal portion 188 adapted to bear against the distal end 138 of the shaft 114, and an inner hollow portion 190 having a diameter slightly larger the that of the distal end of the cutting blade 120.

A core member 192 (FIG. 9B, see also general reference numeral 124) having a distal end 194 and a proximal end 196 extends through the cutter blade 120. Adjacent distal end 194, the core member 192 defines an anvil/support 195 separated from the main body portion 198 of core member 192 by a first circumferential groove or recessed portion 202 (see also general reference numeral 130). It should be understood that the present invention and its related prior art have typically been implemented in a cylindrical geometric format, however, it is not intended that the present invention necessarily be limited in this fashion.

The core member 192 is sized for a relatively tight, but easily sliding, fit through the hollow cutting blade 120 (i.e., such that the longitudinal axes of the cutting blade and of the core member are generally co-axial with respect to one another, and such that the elements are so sized relative to one another that the core essentially freely slides within the cutter—a much wider range of "fits" than that possible in prior art surgical punch devices). By this it is meant to emphasize that since the cutting blade and core are not unduly influenced by aberrations in the alignment of the moving parts of the activation mechanism, adjustments may be made in the gap width between the core and the cutting blade to suit the parameters of the particular usage context desired, i.e., according to the tissue to be cut. A layer of surgically inert lubricating or anti-friction coating material such a silicone lubricant or a Teflon coating (generally indicated at 197) may be disposed on the distal portion of the core to facilitate this sliding fit. Further, the core and the cutting blade both are contemplated to be formed of rigid material such as machined metal. Therefore, the tolerances achievable may be made small resulting much improved co-axial alignment of the elements with a consequent improvement in ease of sliding movement and improved cutting efficiency, if desired. Similarly, a certain amount of increased "play" between the elements also may be achieved to accommodate the nature of the material to be cut without the introduction of core dragging as in the prior art.

Adjacent the proximal end 196 of the core member 192 a second groove 204 separates a proximal portion 206 of the core member from the main body portion 198 thereof. The proximal portion 206 of core member 192 in this embodiment has a smaller diameter than that of the main body portion 198. Further, proximal portion 206 is substantially longer than the comparable portion of the core of prior art devices. (see, FIG. 9B)

Figure 3:
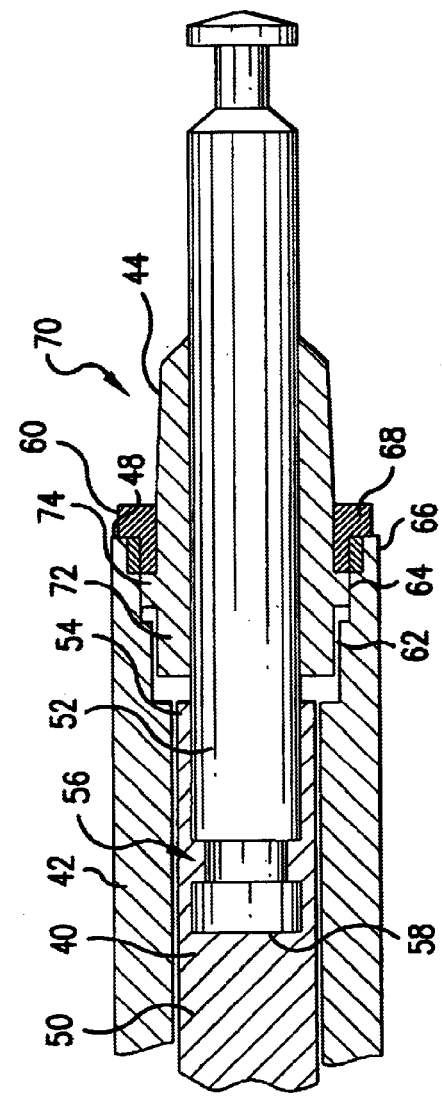
FIG. 3 is a cut away, side cross-sectional view of the distal portion of a prior art surgical punch showing the cutting blade attached in "floating" relationship with the outer sheath portion of an activation mechanism and a rigid core passing through both the outer sheath portion and the cutting blade.
Figure 10:
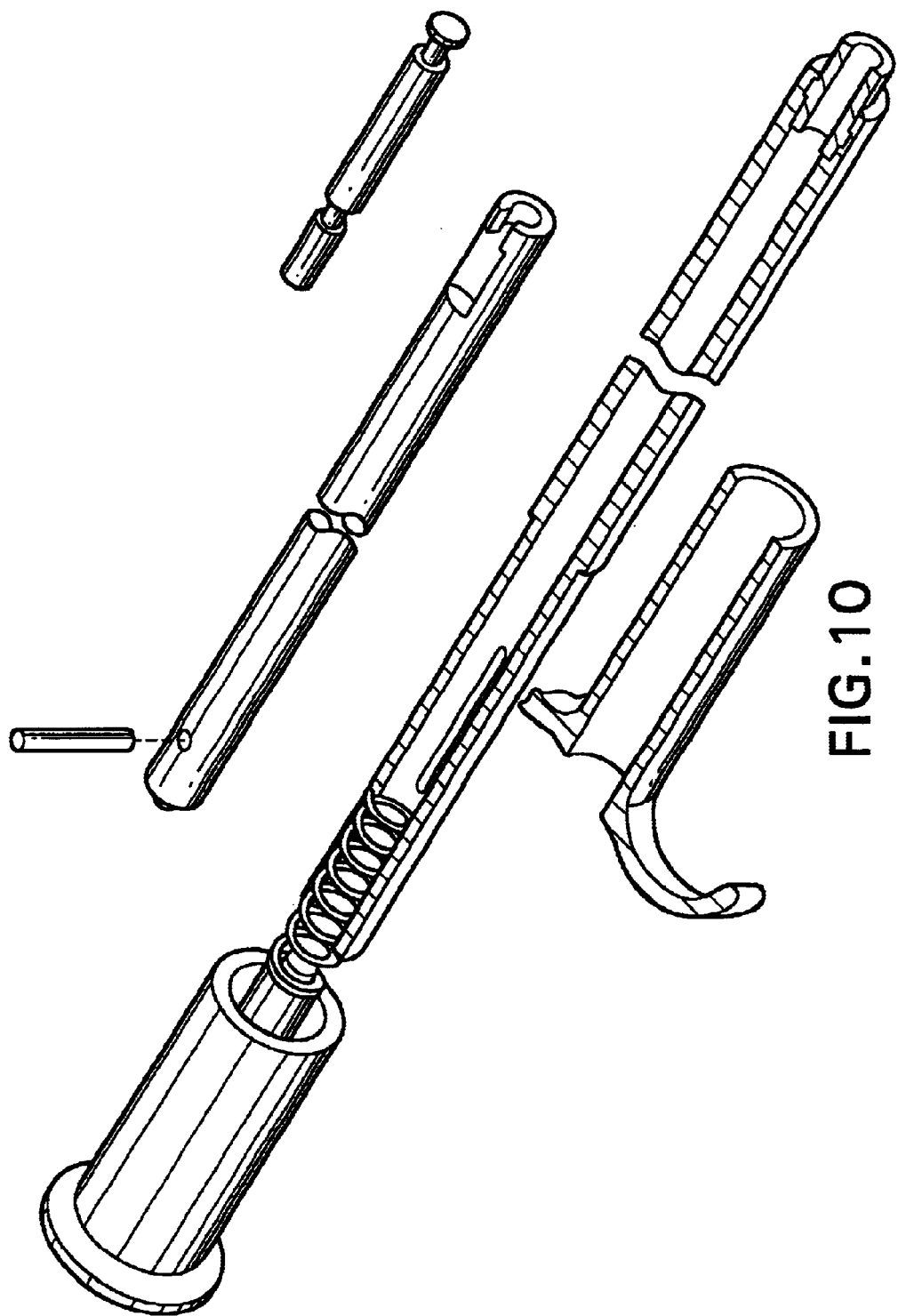
FIG. 10 is an exploded view of another embodiment of a surgical punch device in accordance with the present invention.
Figure 11:
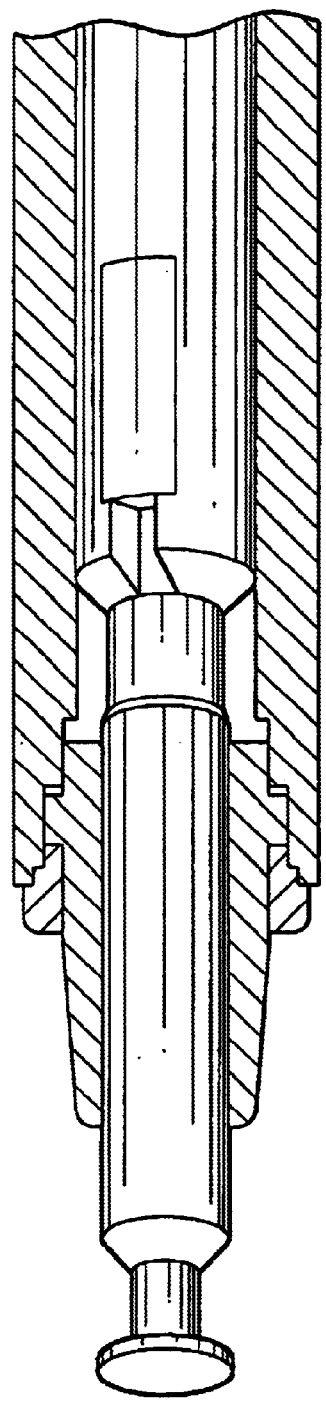
FIG. 11 is a cut away, partial cross-sectional perspective view of the distal portion of the embodiment of the present invention shown in FIG. 10 in its first operative position.
Figure 12:
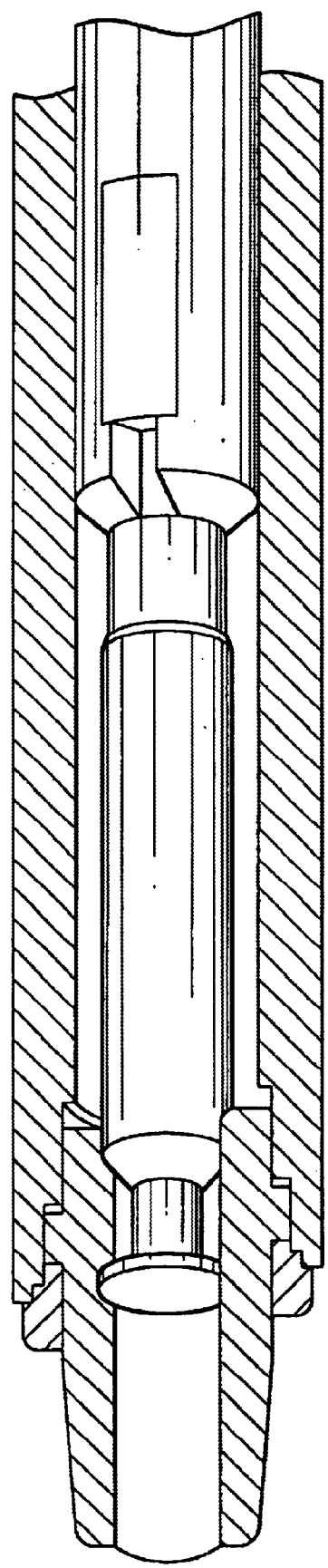
FIG. 12 is a cut away, partial cross-sectional perspective view of the distal portion of the embodiment of the present invention shown in FIG. 10 in its second operative position.

This construction of the core member 192 has been found to facilitate its attachment to the distal end of the rod and to provide other benefits not found in the prior art. Accordingly, as best seen in FIGS. 5, 8, 9A and 9B, instead of forming the core and rod as a single machined metal piece as in the prior art, or by rigidly attaching the proximal portion of a machined metal core to a plastic rod by so-called "insert molding" or the like (see FIG. 3), at least the distal end portion of the rod has been found to be conveniently formed by methods such as injection molding. More specifically, the distal end portion of the rod, which may either be formed integrally with the remainder of the rod or fixedly attached thereto, may take any one of several forms. In the preferred embodiments herein described by way of illustration, the distal end of the rod may include an integral base with a cover portion (FIGS. 9A and 9B) or a partially open sided cavity portion (FIGS. 10–12).

Figure 9A:
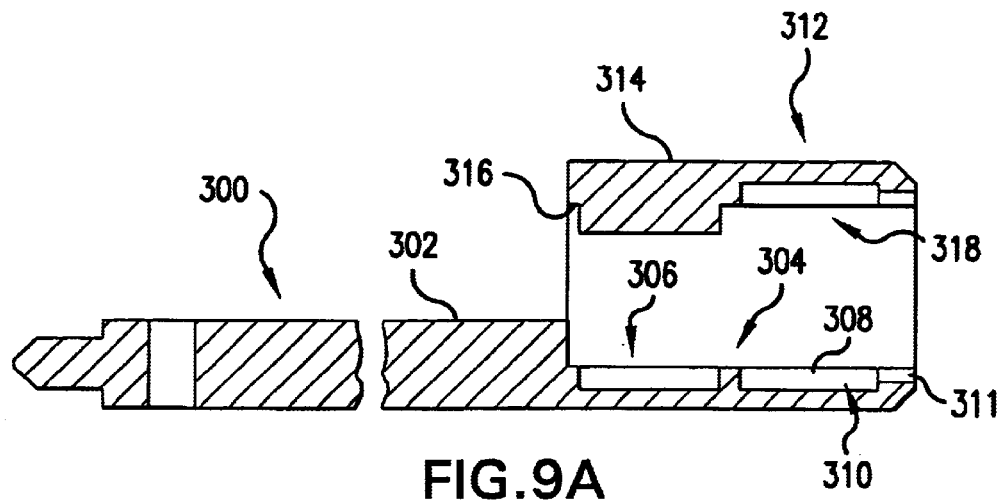
FIG. 9A is an exploded, cross-sectional side view of an internal plunger-like member (rod) of an activation device designed to receive the proximal end of the core of a cutting assembly in "floating" relationship therewith as illustratively shown in FIGS. 5–7.
Figure 9B:
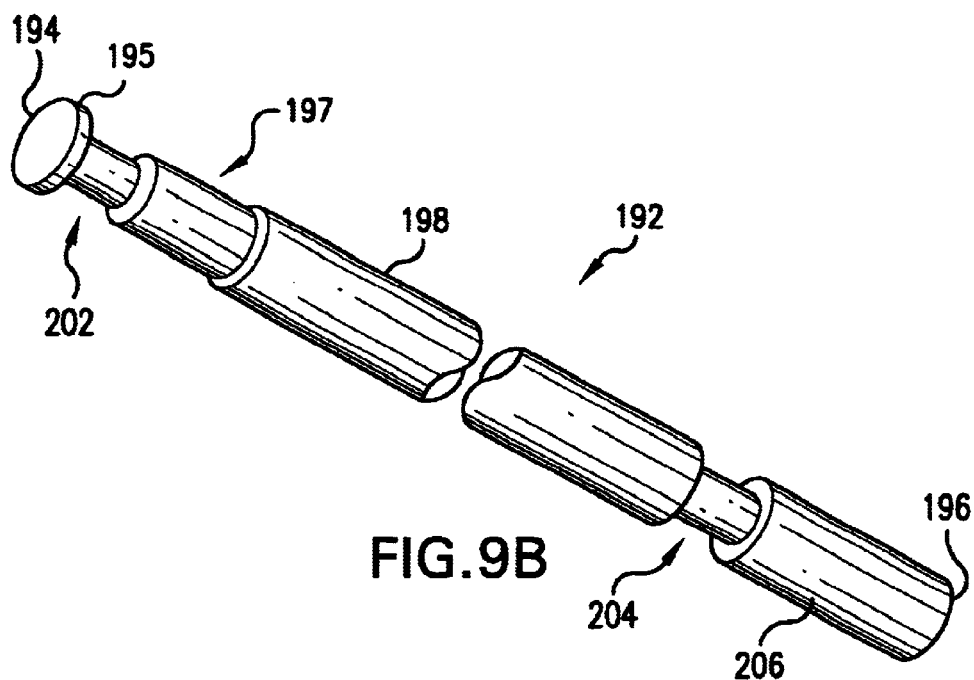
FIG. 9B is an illustrative perspective view of a core suitable for attachment to the distal end of the rod shown in FIG. 9A.

In the integral base with cover alternative, best seen in FIGS. 9A and 9B, the base portion 300 has a cross-section the outer surface 302 of which is sized to slide within the shaft 114. In addition, a substantially flat surface 304 of the base portion 300 defines a pair of longitudinally adjacent, open-topped cavities 306 and 308. In the illustrative embodiment shown, the proximalmost cavity 306 defines a substantially rectangular volume having its longest sides substantially parallel to the longitudinal axis of the rod. The distalmost cavity 308, on the other hand, has a first part 310 adjacent to cavity 308 having a shape longitudinally similar to, but slightly larger than, a longitudinal half of the proximal portion 206 of the core 192. Similarly, the distal part 311 of cavity 310 that connects first cavity part 310 to the distal end of the rod has a shape longitudinally similar to, but slightly larger than, a longitudinal half of the base of the groove 204.

The cover portion 312 also has cross-section the outer curved surface 314 of which is sized to slidingly engage the longitudinal walls of the shaft 114. In addition, the flat surface 316 of the cover portion 312 defines a longitudinally adjacent projection 314 and cavity 318. In the preferred embodiment shown, the projection 314 is proximalmost and defines a substantially rectangular volume comparable to that of cavity 310 wherein its longest sides are substantially parallel to the longitudinal axis of the activation mechanism. The cavity 318, on the other hand, is substantially a mirror image of the cavity 310.

In this illustrative embodiment, therefore, the core portion may be attached to the distal end of the rod by first placing the proximal portion of the machined metallic core into the cavity 310 with the base of the second groove residing in the second part of that cavity. The cover portion 312 then may be placed over the proximal portion of the core member such that the rectangular projection engages the rectangular cavity. Thereafter, the cover portion may be ultrasonically welded in place in engagement with the base portion (see, FIG. 7). In the latter regard, it has been found that the cover portion 312 may be welded to the integral base section either only at the engagement of the rectangular projection with the rectangular cavity, or alternatively, at the engagement of the rectangular cavity and projection and along the sides of the cavity containing the proximal portion of the machined metallic core. In the former alternative, the non-welded distal ends of the integral base portion and the cover portion respectively are three dimensionally curved (see, FIG. 8). The nature of this curvature is designed such that axial pressure exerted against the distal end of the cavity by the proximal portion of the machined metallic core during manipulation of the device will cause the distally three dimensionally curved portions of the non-welded ends of the rod to be deflected outwardly so as to be urged into sliding engagement with the inner walls of the shaft without the introduction of significant resistance to proximal or distal movement of the core within the cutting blade or the rod within the shaft.

Accordingly, it will be understood by those skilled in the art that the size of the cavity containing the proximal portion of the machined metallic core can expand to the limits allowed by the internal walls of the shaft (see, FIG. 8). This expansion of the cavity provides the option of an enlarged quantum of "float" between the rod and the machined metal core. The interrelationship between the shaft and the rod, however, is such that this quantum of cavity expansion is limited. Thus, there is no danger of disengagement of the core from the rod, and the relative movability among the parts of the device as described herein is always maintained.

Alternatively, as illustratively shown in FIGS. 10–12, the distal end of the rod of the activation mechanism may be formed, for example by injection molding, into substantially any other desired shape adapted to "floatingly" hold the proximal portion of the core in/to the distal portion of the rod. Hence, a cavity sized slightly larger than the proximal end of the machined metallic core may be formed adjacent to the distal end of the core. Further that cavity may be connected to the distal end of the core by an axial cavity slightly larger than the second recessed portion of the machined metallic core. In this case, the side walls of the main cavity and the axial cavity may either be cut away or never formed in axial alignment with one another in such a configuration that the proximal portion and second recessed portions of the machined metallic core respectively may be securely, yet "floatingly", snapped into the main and axial cavities at distal end of the plastic rod.

In summary, therefore, it will be understood that the core is allowed to "float" relative to the rod independently at the same time that the cutting blade is allowed to "float" independently relative to the shaft. Therefore, the cutting blade assembly can be made to operate essentially independently of the activation device in terms of the alignment of the relative axes of movement involved. As a result, the device is easier to operate, the phenomenon of dragging is reduced or removed, and the opening formed in the tissue by the device is more accurately and cleanly cut.

Significantly improved formation of holes in interior bodily tissue layers such as those of the aorta may be accomplished with the device herein disclosed. As in the prior art, the anvil portion of the core may be inserted into an incision in the aortic wall such that its proximal end rests against the interior thereof with the first groove portion thereof extending through the incision. At this point, the device may be manipulated so as to move from its first configuration to its second configuration. As it does so the anvil pulls the tissue proximally as the cutting blade slides distally along the outer surface of the core thereby shearing the tissue to form the desired hole.

Also in the prior art, it was found to be advantageous to allow the cutting blade to "float" relative to the elongate hollow member. Hence, it was possible for the device to be somewhat self-aligning in the creation of a hole through a tissue wall against which it bore. However, this self-alignment was of the anvil with the longitudinal passageway through the cutting blade, not necessarily radially and/or angularly relative to the tissue layer being cut. Further, the core still tended to drag along the passageway in the cutting blade making operation of the device difficult. In addition, in order to allow the cutting blade to "float", the clearance between the cutting blade and the core had to be greater than desirable for the creation of a smooth cut, i.e., the gap between the cutting blade and the core had to be large enough to allow the cutting blade axis to deviate somewhat from the device axis for alignment (i.e., because the rod was integrally formed rigidly with the core alignment failures along the shaft interior with the rod adversely impacted the operation of the core in the cutting blade). These structural limitations introduced problems both with the usability of the device and with the quality of the resulting formed holes.

In this invention, making the operative portion of the device substantially totally self-aligning with respect to the activation portion thereof solves these problems. This is because the axis of the cutting blade and the axis of the core member now can both deviate independently relative to the axis of the activation portion thereof. This means that the cut boundaries of a punched out tissue plug can be made smoother because the gap between the core and the cutting blade may be reduced. Further, the operability of the device is facilitated because the core no longer drags along the inner passageway defined by the cutting blade as a result of "play" between the rod and the shaft of the activation mechanism. Finally, the hole formed in the tissue is closer to radial relative to the vessel/organ wall thereby making a secure graft thereto easier to form securely.

Additional advantages over prior art surgical punch devices are also possible by modifications of the configuration of certain internal operating parts of the device disclosed above, and by improvements in the design of the cutting blade edge. These advantages are maximized in the context of the present invention, but also may find use in older devices that do not provide for the separation of the axes of operation of the cutting blade assembly from the axes of operation of the activation mechanism. Specifically, it has been discovered that jamming of a cut out plug within the tool can be avoided or reduced by the internal redesign of certain parts of the device (both with and without the use of surgically inert lubricants or other friction reducing coatings). In addition, a novel cutting edge configuration has been found to improve the shearing of aortal tissue without the need for relative rotation between the inner and outer components or tissue tearing. These advances are described in illustrative preferred forms below.

First, with respect to the reduction of device jamming in connection with the removal of severed tissue from within the tool, it will be understood that the tissue plug removal operation involves the relative movement of the inner core and the cutting blade element from their second relative positions back to their first relative positions after the completion of the punching operation. Compare FIG. 12 with FIG. 11. In theory, this relative movement should occur as a result of simply releasing the pressure applied to the proximal end of the plunger-like element so as to allow the bias of the helical spring of the activation mechanism to return the parts of the device to their first relative positions. In practice, however, this automatic reversal of the positions of the parts often does not occur.

The reasons for this heretofore have not been entirely clear. It now has been recognized, however, that the cause of the jamming phenomena just described may be traced (at least in part) to the presence of excess tissue adjacent the respective distal ends of the sliding engagements of the anvil and/or main body portion of the machined metallic core with the inner walls of the cutting blade passageway. More specifically, as mentioned above, the tissue of the wall of the aorta consists of three layers, the one of which called the "adventitia" being tough and resilient in nature. Accordingly, as the lower surface of the anvil urges the tissue to be punched proximally toward and into the cutting blade passageway, the adventitia tissue tends to stretch prior to being severed. This, in turn, means that a certain quantity of tissue is drawn into (and/or through) the gap between the peripheral edge of the anvil and the adjacent inner wall of the cutting blade passageway prior to the actual severing of the tissue.

After the severing of the punched out tissue, however, the substantially elastic stretching tension on the punched out tissue is released. This creates a quantum of tissue adjacent to the upper outer periphery of the anvil that is substantially thicker than the gap between the side of the anvil and the inner wall of the cutting blade. Hence, as the core attempts to move distally relative to the cutting blade in order to free the punched out tissue plug trapped within the device, the formerly stretched tissue tends to bunch up and bind at the distal opening between the anvil and the cutting blade passageway inner wall.

Further, if the edges of the punched out tissue plug are rough or ragged, parts of these rough or ragged edges have a tendency to lodge between the large diameter main portion of a machined metal core and the inner wall of the cutting blade passageway. Specifically, as the core attempts to move distally relative to the cutting blade to free a punched out tissue plug, the tissue at the distal end of the gap between the large diameter core main portion and the cutting blade passageway also tends to bunch up. This also causes resistance to the free distal movement of the core relative to the cutting blade that may be in excess of the bias of the spring.

Figure 13:
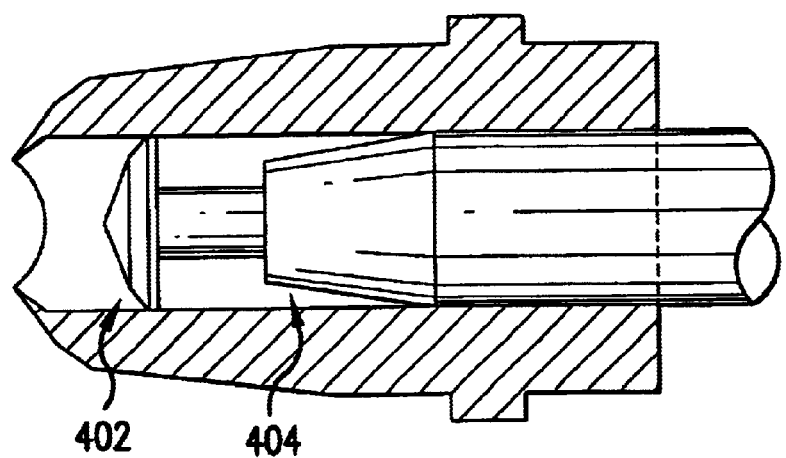
FIG. 13 is a cut away, partial cross-sectional view of an alternative core/rod configuration located within the passageway of a cutting blade in accordance with the present invention.

Once this cause of the above-described jamming problem (which applies both to prior art surgical punch devices and to the improved device discussed above) was understood, it became possible to effectively develop a solution. Thus, since the primary problem appears to be the presence of extra tissue at locations within the device where it has no place to go and thus causes jamming, the design of the internal parts of the device may be changed to accommodate the extra tissue. It has been found that this may be accomplished by the removal of material, preferably in the form of substantially triangular cross-sectional portions, from the distal outer periphery of the anvil portion of the machined metallic core, and from the distal outer periphery of the proximalmost wall of the first recess of the machined metallic core, as illustratively respectively shown at 402 and 404 in FIG. 13.

The key limitation on this solution to the jamming problem is that the amount of material removed from the exterior walls of the core cannot be such as to adversely impact the alignment of the cutting blade and its associated inner core member. Obviously, this limitation is more important as it applies to the improved surgical punch device described above because the cutting blade and its associated inner core in that device "float" substantially independently with respect to the portions of the activation mechanism to which they are attached. Nevertheless, as long as this limitation is maintained, the removed material from the inner core provides circumferential channels between the inner core and the cutting blade passageway adapted to contain the extra bunched up tissue and to alleviate resistance to distal movement of the core relative to the cutting blade passageway.

Of course, in those cases in which resistance to the automatic return of the parts to their normal positions relative to one another is still present between the inner core and the trapped tissue despite the design changes just discussed, appropriate surgically inert lubricants or other friction reducing coatings may be applied to the surfaces of the core that will come into contact with the tissue during the punching procedure to further facilitate the relative movement of the respective parts of the device. Surgically inert lubricant materials, such as Dow Corning Medical Fluid No. 360 or the like, have been found to be suitable for this purpose. Similarly, the application of Teflon or similar non-sticking agents to the outer surfaces of the inner core are acceptable, although somewhat more costly.

Figure 14:
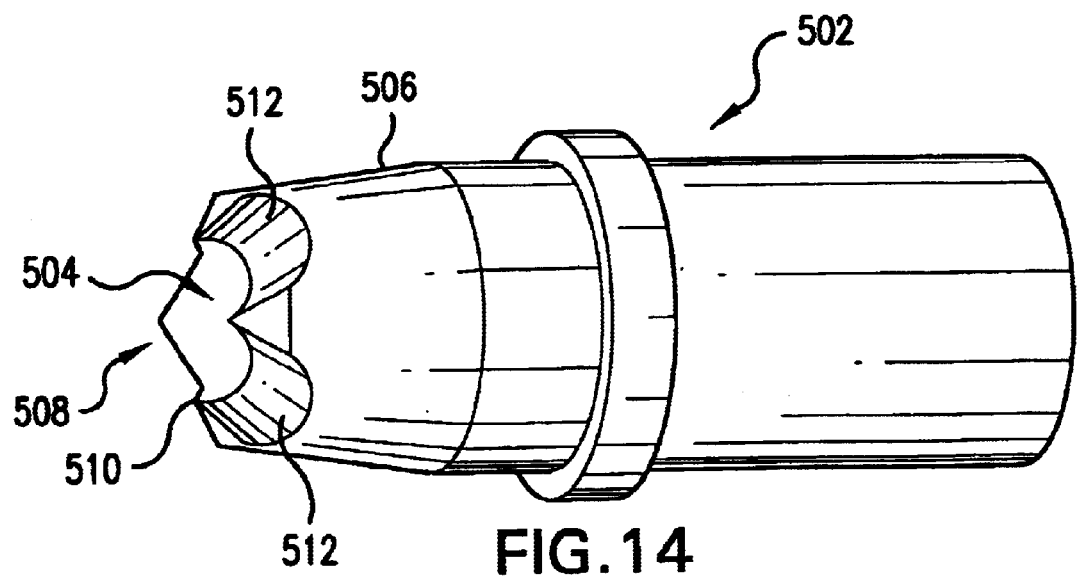
FIG. 14 is a perspective view of an alternative cutting blade member configuration in accordance with the present invention.

Similarly, the cutting blade edge design illustratively shown in FIG. 14 improves shear cutting. More specifically, a surgical punch device including this improvement includes a body 502 defining a longitudinal passageway 504 having an end portion 506. This end portion includes a plurality of longitudinally outwardly extending tissue-piercing members 508 disposed in substantially equally circumferentially spaced relationship to one another. Further, each said tissue-piercing member has a longitudinally outwardly facing point 510, and a longitudinally outwardly facing cutting edge 512 is located between each adjacent pair of longitudinally outwardly facing points along corresponding inwardly extending curves. This structure allows a layer of tissue that is urged inwardly against the end portion of the body to be first pierced by the points, and thereafter, sheared longitudinally and circumferentially relative to each pierced portion thereof.

More particularly, starting from the conventional circular cutting edge disposed in a plane perpendicular to the axis of the cutting blade, a preselected number of point locations may be selected (usually in substantially equally spaced relation to one another) about the periphery of the cutting edge. Thereafter, material may be removed from the cutting blade element between the preselected points such that corresponding new curved cutting blade edges are formed between each pair of preselected points. Each of the corresponding new curved cutting blade edges follows the inner wall of the cutting blade element in circumferential relation to the cutting blade as well as a corresponding curve in axial relation to the cutting blade.

In this way what may be referred to as a "scalloped" cutting blade edge may be created at the distal end of the cutting blade, with each scallop being the same as those adjacent thereto. The concept of this embodiment is that the various points will tend to pierce the tough and resilient tissue layer of the aorta wall, and that the cutting edges between the points thereafter will sever the aorta wall tissue layers between the pierced locations. Hence, the aorta wall tissue will be more accurately and cleanly severed, rather than stretched, by the cutting blade assembly. Also, the tissue plugs will be punched out with cleaner edges under the exertion of less applied force. Still further, a cutting edge similar to that just described (not shown) may be formed along the outer proximal edge of the anvil either alone, or in combination with, the above-described cutting blade configuration, if desired. In such a case, however, care must be exercised to insure that the respective longitudinal axes of the cutter passageway and the inner core remain closely enough aligned with one another that the cutting edges do not interfere with the reciprocal movement of the inner core relative to the cutter passageway.

Having thus described a preferred embodiments of the invention and their method of operation, numerous variations, alterations, changes, modifications and the like will occur to those skilled in the art without departure from the present invention in its broadest aspects. Accordingly, it will be understood that the foregoing specification has been presented by way of illustration only, and not by way of limitation. It is intended that the scope of the present invention be limited only by the terms of the appended claims.

What is claimed is:

1. A surgical tissue punch device comprising:
   a tissue cutting assembly attached to an activation device;
      said tissue cutting assembly including:
      (i) a body having a body proximal end portion, a body distal end portion and a longitudinal passageway having a first longitudinal length extending between said body proximal end portion and said body distal end portion, said body distal end portion including a distally facing cutting blade edge adjacent said passageway, and (ii) an elongate core member having a core proximal end portion, a core distal end portion, and a second longitudinal length greater than said first longitudinal length, said elongate core member being disposed in reciprocally movable relationship with said body in said longitudinal passageway, said core member defining a substantially circumferentially oriented recessed tissue engagement portion in closely spaced relation to said core distal end portion;

said activation device including means for moving said body and said core reciprocally relative to one another between a first position wherein a distal portion of said core including said recessed portion extends substantially longitudinally and distally of said cutting blade edge, and a second position wherein said distal portion of said core resides within said passageway;

wherein said passageway of said body and said core are sized relative to one another such that a portion of at least one bodily tissue layer located in said recessed portion when said tissue cutting assembly is disposed in said first position is sheared away from the tissue adjacent thereto by said cutting blade as said core and said body are moved from said first position to said second position relative to one another; and further wherein said core and said body are attached separately to said activation device such that said body and said core may shift radially and/or longitudinally relative to each other and to said activation device; and wherein at least the portion of the outer surface of said elongate core member that extends outwardly from said distal end of said passageway in said first position of said device is provided with a surgically inert friction reducing coating.

2. A surgical punch according to claim 1, wherein:

said body defines a distal end portion including a plurality of longitudinally outwardly extending tissue piercing members disposed in substantially equally circumferentially spaced relationship to one another, each said tissue piercing member having a longitudinally outwardly facing point, and a longitudinally outwardly facing cutting edge located between each adjacent pair of longitudinally outwardly facing points along corresponding generally proximally extending curves, whereby a layer of tissue urged proximally against said distal end portion of said body is first pierced by said points, and thereafter is sheared longitudinally and circumferentially relative to each pierced portion thereof; and wherein at least the portion of the outer surface of said elongate core member that extends outwardly from said distal end of said passageway in said first position of said device is provided with a surgically inert friction reducing coating.

3. A surgical punch according to claim 2, wherein:

said activation means comprises an elongate sheath having a sheath proximal end portion, a sheath distal end portion and defines a longitudinal passageway between said sheath proximal end portion and said sheath distal end portion; a rod having a rod distal end portion and a rod proximal end portion disposed for reciprocal movement in said longitudinal passageway of said sheath, means associated with said sheath proximal end portion for floatingly attaching said sheath distal end portion to said body, and means associated with said rod proximal end portion for floatingly attaching said rod distal end portion to said core proximal end portion.

4. The surgical punch according to claim 3, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover the distal end portion of said sheath and to allow the sharpened distal core end portion of said body to extend therethrough outwardly of said sheath distal end portion;

whereby said body may be floatingly mounted to said sheath distal end portion for limited shifting movement longitudinally and radially relative thereto.

5. The surgical punch according to claim 3, wherein:

said elongate core member defines a second recessed area substantially adjacent said proximal core end portion and the transverse cross-sectional area of the portion of said elongate core member between said second recessed portion and said proximal core end portion is smaller than the remainder of the non-recessed portion of said elongate core member, and said distal rod end portion defines a cavity extending proximally into said rod, said cavity being of substantially the same shape, but slightly longitudinally and radially larger than, said second recessed portion of said elongate core member and said portion of said elongate core member between said second recessed portion and said proximal core end portion, and means for locating said second recessed portion of said elongate core member and said portion extending proximally therefrom into said cavity;

whereby said cavity securely retains said second recessed portion and the part of said elongate core member extending proximally therefrom in floating relation to said rod such that said elongate core member may move to a limited extent both longitudinally and radially relative to said distal end portion of said rod.

6. The surgical punch device according to claim 3, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover said sheath distal end portion and to allow the sharpened body distal end portion to extend therethrough outwardly of said sheath distal end portion;

whereby said body may be floatingly mounted to said sheath distal end portion for limited shifting movement longitudinally and radially relative thereto; and said elongate core member defines a second recessed area substantially adjacent said proximal core end portion and a transverse cross-sectional area of the portion of said elongate core member between said second recessed portion and said proximal core end portion is smaller than the remainder of the non-recessed portion of said elongate core member; and said distal rod end portion defines a cavity extending proximally into said rod, said cavity being of substantially the same shape, but slightly longitudinally and radially larger than, said second recessed portion of said elongate core member and the portion of said elongate core member between said second recessed portion and said proximal core end portion, and means for locating said second recessed portion of said elongate core member and the portion extending proximally therefrom in said cavity;

whereby said cavity securely retains said second recessed portion and the part of the core extending proximally therefrom in floating relation to said rod such that said elongate core member may move to a limited extent both longitudinally and radially relative to said rod distal end.

7. A surgical punch according to claim 1, wherein said main body and said longitudinal passageway are co-axially cylindrical and circular in transverse cross-section respectively.

8. A surgical punch according to claim 7, wherein:

said activation means comprises an elongate sheath having a sheath proximal end portion, a sheath distal end portion and defines a longitudinal passageway between said sheath proximal end portion and said sheath distal end portion; a rod having a rod distal end portion and a rod proximal end portion disposed for reciprocal movement in said longitudinal passageway of said sheath, means associated with said sheath proximal end portion for floatingly attaching said sheath distal end portion to said body, and means associated with said rod proximal end portion for floatingly attaching said rod distal end portion to said core proximal end portion.

9. The surgical punch according to claim 8, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover the distal end portion of said sheath and to allow the sharpened distal core end portion of said body to extend therethrough outwardly of said sheath distal end portion;

whereby said body may be floatingly mounted to said sheath distal end portion for limited shifting movement longitudinally and radially relative thereto.

10. The surgical punch according to claim 8, wherein:

said elongate core member defines a second recessed area substantially adjacent said proximal core end portion and the transverse cross-sectional area of the portion of said elongate core member between said second recessed portion and said proximal core end portion is smaller than the remainder of the non-recessed portion of said elongate core member; and said distal rod end portion defines a cavity extending proximally into said rod, said cavity being of substantially the same shape, but slightly longitudinally and radially larger than, said second recessed portion of said elongate core member and said portion of said elongate core member between said second recessed portion and said proximal core end portion, and means for locating said second recessed portion of said elongate core member and said portion extending proximally therefrom into said cavity;

whereby said cavity securely retains said second recessed portion and the part of said elongate core member extending proximally therefrom in floating relation to said rod such that said elongate core member may move to a limited extent both longitudinally and radially relative to said distal end portion of said rod.

11. The surgical punch device according to claim 8, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover said sheath distal end portion and to allow the sharpened body distal end portion to extend therethrough outwardly of said sheath distal end portion;

whereby said body may be floatingly mounted to said sheath distal end portion for limited shifting movement longitudinally and radially relative thereto; and said elongate core member defines a second recessed area substantially adjacent said proximal core end portion and a transverse cross-sectional area of the portion of said elongate core member between said second recessed portion and said proximal core end portion is smaller than the remainder of the non-recessed portion of said elongate core member; and said distal rod end portion defines a cavity extending proximally into said rod, said cavity being of substantially the same shape, but slightly longitudinally and radially larger than, said second recessed portion of said elongate core member and the portion of said elongate core member between said second recessed portion and said proximal core end portion, and means for locating said second recessed portion of said elongate core member and the portion extending proximally therefrom in said cavity;

whereby said cavity securely retains said second recessed portion and the part of the core extending proximally therefrom in floating relation to said rod such that said elongate core member may move to a limited extent both longitudinally and radially relative to said rod distal end.

12. A surgical punch device according to claim 1, wherein:

said distal portion of said elongate core member defines (i) a first circumferential channel portion at the periphery of said core distal end portion, said channel having a generally proximally extending, substantially triangular cross-section, and (ii) a second circumferential channel portion at the outer periphery of a proximal edge of said recessed portion, said second channel portion having a generally proximally extending, substantially triangular cross-section;

whereby a plug of tissue having a frayed or rough outer periphery disposed in said recessed portion when said elongate core member and said body are is in their second position will not significantly impede the movement of said elongate core member toward its first position relative to said body.

13. A surgical punch according to claim 12, wherein:

said activation means comprises an elongate sheath having a sheath proximal end portion, a sheath distal end portion and defines a longitudinal passageway between said sheath proximal end portion and said sheath distal end portion; a rod having a rod distal end portion and a rod proximal end portion disposed for reciprocal movement in said longitudinal passageway of said sheath, means associated with said sheath proximal end portion for floatingly attaching said sheath distal end portion to said body, and means associated with said rod proximal end portion for floatingly attaching said rod distal end portion to said core proximal end portion.

14. The surgical punch according to claim 13, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover the distal end portion of said sheath and to allow the sharpened distal core end portion of said body to extend therethrough outwardly of said sheath distal end portion;

whereby said body may be floatingly mounted to said sheath distal end portion for limited shifting movement longitudinally and radially relative thereto.

15. The surgical punch according to claim 13, wherein:

said elongate core member defines a second recessed area substantially adjacent said proximal core end portion and the transverse cross-sectional area of the portion of said elongate core member between said second recessed portion and said proximal core end portion is smaller than the remainder of the non-recessed portion of said elongate core member; and said distal rod end portion defines a cavity extending proximally into said rod, said cavity being of substantially the same shape, but slightly longitudinally and radially larger than, said second recessed portion of said elongate core member and said portion of said elongate core member between said second recessed portion and said proximal core end portion, and means for locating said second recessed portion of said elongate core member and said portion extending proximally therefrom into said cavity;

whereby said cavity securely retains said second recessed portion and the part of said elongate core member extending proximally therefrom in floating relation to said rod such that said elongate core member may move to a limited extent both longitudinally and radially relative to said distal end portion of said rod.

16. The surgical punch device according to claim 13, wherein:

said body has a substantially constant exterior transverse cross-section and a circumferentially located outwardly projecting portion at a predetermined position along its length;

said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and said device further comprises a ring cap adapted to tightly fit into said outermost counterbore, to cover said sheath distal end portion and to allow the sharpened body distal end portion to extend therethrough outwardly of said sheath distal end portion;

whereby said body may be floatingly mounted to said sheath distal end portion for limited shifting movement longitudinally and radially relative thereto; and said elongate core member defines a second recessed area substantially adjacent said proximal core end portion and a transverse cross-sectional area of the portion of said elongate core member between said second recessed portion and said proximal core end portion is smaller than the remainder of the non-recessed portion of said elongate core member; and said distal rod end portion defines a cavity extending proximally into said rod, said cavity being of substantially the same shape, but slightly longitudinally and radially larger than, said second recessed portion of said elongate core member and the portion of said elongate core member between said second recessed portion and said proximal core end portion, and means for locating said second recessed portion of said elongate core member and the portion extending proximally therefrom in said cavity;

whereby said cavity securely retains said second recessed portion and the part of the core extending proximally therefrom in floating relation to said rod such that said elongate core member may move to a limited extent both longitudinally and radially relative to said rod distal end.

17. A surgical punch according to claim 1, wherein:
said activation means comprises an elongate sheath having a sheath proximal end portion, a sheath distal end portion and defines a longitudinal passageway between said sheath proximal end portion and said sheath distal end portion; a rod having a rod distal end portion and a rod proximal end portion disposed for reciprocal movement in said longitudinal passageway of said sheath, means associated with said sheath proximal end portion for floatingly attaching said sheath distal end portion to said body, and means associated with said rod proximal end portion for floatingly attaching said rod distal end portion to said core proximal end portion.

18. The surgical punch according to claim 17, wherein:
said body has a substantially constant exterior transverse cross-section and a circumferentially located outwardly projecting portion at a predetermined position along its length;
said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and
said device further comprises a ring cap adapted to tightly fit into said outermost counterbore, to cover the distal end portion of said sheath and to allow the sharpened distal core end portion of said body to extend therethrough outwardly of said sheath distal end portion;
whereby said body may be floatingly mounted to said sheath distal end portion for limited shifting movement longitudinally and radially relative thereto.

19. The surgical punch according to claim 17, wherein:
said elongate core member defines a second recessed area substantially adjacent said proximal core end portion and the transverse cross-sectional area of the portion of said elongate core member between said second recessed portion and said proximal core end portion is smaller than the remainder of the non-recessed portion of said elongate core member; and
said distal rod end portion defines a cavity extending proximally into said rod, said cavity being of substantially the same shape, but slightly longitudinally and radially larger than, said second recessed portion of said elongate core member and said portion of said elongate core member between said second recessed portion and said proximal core end portion, and means for locating said second recessed portion of said elongate core member and said portion extending proximally therefrom into said cavity;
whereby said cavity securely retains said second recessed portion and the part of said elongate core member extending proximally therefrom in floating relation to said rod such that said elongate core member may move to a limited extent both longitudinally and radially relative to said distal end portion of said rod.

20. The surgical punch device according to claim 17, wherein:
said body has a substantially constant exterior transverse cross-section and a circumferentially located outwardly projecting portion at a predetermined position along its length;
said sheath defines at least outermost, an innermost and intermediate counterbores extending proximally into its distal end portion, said innermost counterbore being longer and having a smaller diameter than the intermediate counterbore adjacent thereto, said intermediate counterbores being successively longer and having a smaller diameter than the one of said intermediate counterbores outwardly adjacent thereto, and said outermost counterbore being shorter and having a larger diameter than any of the others of said counterbores; and
said device further comprises a ring cap adapted to tightly fit into said outermost counterbore, to cover said sheath distal end portion and to allow the sharpened body distal end portion to extend therethrough outwardly of said sheath distal end portion;
whereby said body may be floatingly mounted to said sheath distal end portion for limited shifting movement longitudinally and radially relative thereto; and
said elongate core member defines a second recessed area substantially adjacent said proximal core end portion and a transverse cross-sectional area of the portion of said elongate core member between said second recessed portion and said proximal core end portion is smaller than the remainder of the non-recessed portion of said elongate core member; and
said distal rod end portion defines a cavity extending proximally into said rod, said cavity being of substantially the same shape, but slightly longitudinally and radially larger than, said second recessed portion of said elongate core member and the portion of said elongate core member between said second recessed portion and said proximal core end portion, and means for locating said second recessed portion of said elongate core member and the portion extending proximally therefrom in said cavity;
whereby said cavity securely retains said second recessed portion and the part of the core extending proximally therefrom in floating relation to said rod such that said elongate core member may move to a limited extent both longitudinally and radially relative to said rod distal end.

21. A surgical punch device comprising:
a main body having a first distal end portion, said body defining a longitudinal passageway opening into said distal end portion so as to form a sharp circumferential edge at the joinder of said passageway and said first distal end portion; and
an elongate member including a second distal end portion and a distal section proximally adjacent to said second distal end portion, said elongate member being disposed in reciprocally movable relation within said passageway such that said distal section of said elongate member may move between a first position wherein said distal section extends distally outwardly relative to said distal end portion of said main body and a second position wherein said distal portion of said elongate member is disposed within said passageway;
said distal section of said elongate member defining (i) a circumferential recessed portion disposed in spaced relationship to said second distal end portion, (ii) a first circumferential channel portion at the periphery of said second distal end portion, said channel having a generally proximally extending, substantially triangular cross-section, and (iii) a second circumferential channel portion at the outer periphery of a proximal edge of said recessed portion, said second channel portion having a generally proximally extending, substantially triangular cross-section;

whereby a plug of tissue having a frayed or rough outer periphery disposed in said recessed portion when said elongate member and said main body are in their second position will not significantly impede the movement of said elongate member toward its first position relative to said main body; and wherein at least said distal section of said elongate member is coated with a surgically inert friction reducing material.

22. A surgical punch device comprising:

a main body having a first distal end portion, said body defining a longitudinal passageway opening into said distal end portion so as to form a sharp circumferential edge at the joinder of said passageway and said first distal end portion; and an elongate member including a second distal end portion and a distal section proximally adjacent to said second distal end portion, said elongate member being disposed in reciprocally movable relation within said passageway such that said distal section of said member may move between a first position wherein said distal section extends distally outwardly relative to said first distal end portion of said main body and a second position wherein said distal section of said elongate member is disposed within said passageway, and said distal section of said elongate member defines a circumferential recessed portion disposed in spaced relationship to said second distal end portion; and wherein said sharp circumferential cutting edge includes a plurality of longitudinally outwardly extending tissue piercing members disposed in substantially equally circumferentially spaced relationship to one another, each said tissue piercing member having a longitudinally outwardly facing point, and a longitudinally outwardly facing cutting edge located between each adjacent pair of longitudinally outwardly facing points along corresponding generally proximally extending curves, whereby a layer of tissue urged proximally against said first distal end portion of said main body is first pierced by said points, and thereafter is sheared longitudinally and circumferentially relative to each pierced portion thereof; and wherein at least said distal section of said elongate member is coated with a surgically inert friction reducing material.

* * * * *